United States Patent [19]
Breton et al.

[11] Patent Number: 6,124,364
[45] Date of Patent: *Sep. 26, 2000

[54] DESQUAMATION/EPIDERMAL RENEWAL OF THE SKIN AND/OR COMBATING SKIN AGING

[75] Inventors: Lionel Breton, Versailles; Nathalie Pineau, Poitiers, both of France

[73] Assignee: Societe L'Oreal S.A., Paris, France

[*] Notice: This patent is subject to a terminal disclaimer.

[21] Appl. No.: 09/288,625

[22] Filed: Apr. 9, 1999

[30] Foreign Application Priority Data

Apr. 10, 1998 [FR] France .................................. 98-04569

[51] Int. Cl.⁷ ...................................... A61K 31/05
[52] U.S. Cl. ............................. 514/733; 514/734
[58] Field of Search ................ 514/2, 646, 520, 514/77, 733, 734; 424/401; 435/6

[56] References Cited

U.S. PATENT DOCUMENTS

| | | |
|---|---|---|
| 5,430,062 | 7/1995 | Cushman et al. |
| 5,616,332 | 4/1997 | Herstein ........................... 424/401 |
| 5,652,228 | 7/1997 | Bissett ............................. 514/77 |
| 5,723,291 | 3/1998 | Kushner et al. ................... 435/6 |
| 5,733,558 | 3/1998 | Breton et al. ..................... 424/401 |
| 5,780,042 | 7/1998 | Gers-Barlag et al. ............. 424/401 |
| 5,837,224 | 11/1998 | Voorhees et al. ................ 424/59 |
| 5,840,681 | 11/1998 | Hersh et al. ..................... 514/8 |

FOREIGN PATENT DOCUMENTS

| | | |
|---|---|---|
| 904774 | 9/1997 | European Pat. Off. ......... A61K 7/48 |
| 64-38009 | 2/1989 | Japan . |
| 8-175960 | 7/1996 | Japan . |

OTHER PUBLICATIONS

Cacazza et al., Patent abstract, EP 773020, (May 1997).

*Primary Examiner*—William R. A. Jarvis
*Assistant Examiner*—Vickie Kim
*Attorney, Agent, or Firm*—Burns, Doane, Swecker & Mathis, L.L.P.

[57] ABSTRACT

The hydroxystilbenes are well suited for promoting desquamation and/or stimulating epidermal renewal and/or combating intrinsic/extrinsic aging of the skin of a human subject in need of such treatment, by topically applying thereto, for such period of time as required to elicit the desired response, a therapeutically effective amount of at least one of said hydroxystilbenes.

12 Claims, No Drawings

DESQUAMATION/EPIDERMAL RENEWAL OF THE SKIN AND/OR COMBATING SKIN AGING

CROSS-REFERENCE TO PRIORITY APPLICATION

This application claims priority under 35 U.S.C. §119 of FR-98/04569, filed Apr. 10, 1998, hereby expressly incorporated by reference.

CROSS-REFERENCE TO COMPANION APPLICATIONS

Copending applications Ser. No. 07/288,626 [Attorney Docket No. 016800-283] and Ser. No. 09/288,624 [Attorney Docket No. 016800-286], both filed concurrently herewith and both assigned to the assignee hereof.

BACKGROUND OF THE INVENTION

1. Technical Field of the Invention

The present invention relates to promoting desquamation of the skin and/or stimulating epidermal renewal and/or combating skin aging by topical application thereto of at least one hydroxystilbene compound/composition.

The compounds/compositions of this invention are especially well suited for promoting desquamation of the skin and/or stimulating epidermal renewal and/or combating intrinsic and/or extrinsic skin aging, as well as for nontherapeutically treating the skin to promote desquamation and/or combat skin aging.

2. Description of the Prior Art

Desquamation is a natural phenomenon linked to the fact that the epidermis, which constitutes the upper layer of the skin, is constantly being regenerated. The epidermis consists of several layers of cells, of which the deepest is the basal layer consisting of undifferentiated cells. Over time, these cells will differentiate and migrate to the surface of the epidermis, constituting various layers thereof, until the corneocytes, which are dead cells which are eliminated by desquamation, are formed at the surface of the epidermis. This loss at the surface of the skin is compensated by the migration of cells from the basal layer to the surface of the epidermis. It entails the perpetual renewal of the skin. The forced elimination of the horny layer accelerates epidermal renewal and makes it possible to combat aging.

At the same time, these cells continue their differentiation, of which the last stage is the corneocyte. These are dead cells which constitute the last layer of the epidermis, namely, the outermost layer also known as the stratum corneum.

Skin aging, resulting from the effects of intrinsic or extrinsic factors on the skin, results in the appearance of wrinkles and fine lines, in yellowing of the skin, which develops in particular a shrivelled appearance, possibly accompanied by the appearance of pigmentation marks, in the disorganization of the elastin fibers and of collagen causing a loss of elasticity, suppleness and firmness and in the appearance of telangiectasia.

Certain of these signs of aging are more particularly linked to intrinsic or physiological aging, namely, to "normal" age-related or chronobiological aging, whereas others are more specific to extrinsic aging, namely, aging generally caused by the environment; this is more particularly photoaging due to exposure to the sun, to light or to any other radiation.

The present invention relates to not only intrinsic or physiological aging, but also to extrinsic aging.

Changes in the skin due to intrinsic aging are the consequence of a genetically programmed aging in which endogenous factors are involved. This intrinsic aging causes, in particular, a slowing down of the renewal of the skin cells, which essentially results in the appearance of clinical alterations such as the reduction in the subcutaneous adipose tissue and the appearance of fine wrinkles or fine lines, and in histopathological changes such as an increase in the number and thickness of the elastic fibers, a loss of vertical fibers of the membrane of the elastic tissue, and the presence of large irregular fibroblasts in the cells of this elastic tissue.

By contrast, extrinsic aging causes clinical alterations such as thick wrinkles and the formation of a soft and/or tanned skin, and histopathological changes such as an excessive accumulation of elastic material in the upper dermis and degeneration of the collagen fibers.

Various active agents suggested for combating skin aging are known to this art.

Thus, U.S. Pat. No. 4,603,146 describes the use of retinoic acid and derivatives thereof in cosmetic compositions for combating skin aging.

Moreover, numerous patents and publications (see, for example, EP-A-413528) describe, and numerous commercially available cosmetic compositions include, α-hydroxy acids such as lactic acid, glycolic acid or citric acid for treating skin aging.

Too, the beta-hydroxy acids and more especially salicylic acid, as well as the derivatives thereof, are known for their desquamative properties (see WO-A-93/10756 and U.S. Pat. No. 4,767,750).

All of the aforesaid prior art compounds elicit action against skin aging by promoting desquamation, namely, the elimination of the "dead" cells situated at the surface of the horny layer of the epidermis. This "desquamative" property is also deemed, often wrongly, "keratolytic" activity.

However, the prior art compounds also present objectionable side effects such as pricking, twitching, overheating and/or redness which are unpleasant for the user.

Need therefore continues to exist for antiaging agents having an action which is at least as effective as that of the prior art compounds, but which do not present the disadvantages thereof.

SUMMARY OF THE INVENTION

Accordingly, a major object of the present invention is the provision of active agents for promoting desquamation of the skin and/or stimulating epidermal renewal, while at the same time avoiding the pricking, twitching, overheating or redness which are unpleasant for the user and which to date have characterized the state of this art.

Briefly, it has now surprisingly and unexpectedly been determined that topically applying an effective amount of at least one hydroxystilbene onto the skin promotes the desquamation thereof and/or stimulates epidermal renewal and therefore combats skin aging.

The hydroxystilbenes according to the present invention advantageously are compounds having the following structural formula (I):

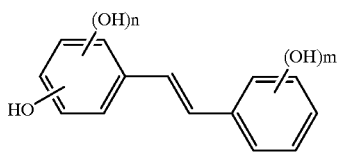

(I)

in which n is an integer ranging from 0 to 4, inclusive, and m is an integer ranging from 0 to 5, inclusive. These compounds may be in a cis- or trans-configuration.

According to the invention, by the term hydroxystilbene are intended both the compounds of formula (I) and the hydroxyalkylated derivatives thereof.

DETAILED DESCRIPTION OF BEST MODE AND SPECIFIC/PREFERRED EMBODIMENTS OF THE INVENTION

More particularly according to the present invention, the hydroxystilbenes are compounds which exist in the natural state in plants of the class of spermatophytes and particularly in grapevines and grapes and in wine.

In the prior art, the hydroxystilbenes are used, inter alia, as depigmenting agents (JP-87/192040), as vasodilating agents (EP-96/830517), as antithrombotic agents (JP-05/016413), in the treatment of various cardiovascular conditions (CA-2187990), as mutagenesis-inhibiting agents (JP-06/024967), or, alternatively, are described as antioxidants.

Among these compounds, resveratrol or (3,4',5-trihydroxystilbene) is of particular interest for the activities described above mainly because it is a natural compound which exists in grape skin and in wine. In this regard, the review by Soleas et al., *Clinical Biochemistry*, vol. 30, No. 2, pp. 91–113, (1997) perfectly summarizes the state of the art regarding this compound and the hydroxystilbenes generically.

However, to date the capacity of the hydroxystilbenes to promote desquamation of the skin and/or stimulate epidermal renewal and/or combat intrinsic and/or extrinsic skin aging was unknown.

The present invention therefore features the use of an effective amount of at least one hydroxystilbene, or composition comprised thereof, to promote desquamation of the skin and/or stimulate epidermal renewal and/or combat intrinsic and/or extrinsic skin aging.

Such compositions are preferably cosmetic or dermatological, advantageously cosmetic compositions.

Among the hydroxystilbenes, particularly representative are the mono-, di-, tri-, tetra-, penta-, hexa-, hepta-, octa-, nonahydroxystilbenes, as well as the hydroxyalkylated derivatives thereof.

By "active ingredient" or "active agent" is intended any molecule, substrate or composition capable of modifying or of modulating the functioning of at least one given biological system.

This invention also features, as an active ingredient, or for the formulation of a composition, an effective amount of at least one hydroxystilbene for promoting desquamation of the skin and/or stimulating epidermal renewal and/or combating intrinsic and/or extrinsic skin aging.

The present invention also features a nontherapeutic regime/regimen for treating the skin to promote desquamation and/or stimulate epidermal renewal and/or combat intrinsic and/or extrinsic aging thereof, by topically applying to the skin an effective amount of at least one hydroxystilbene or cosmetic composition comprising same.

According to the invention, the hydroxystilbenes may be used either alone or in the form of mixtures of any type and may be natural or synthetic in origin.

Advantageously, the hydroxystilbenes according to the invention are selected from among:
4'-hydroxystilbene,
2',4'-dihydroxystilbene,
3',4'-dihydroxystilbene,
4,4'-dihydroxystilbene,
2',4',4-trihydroxystilbene,
3',4',4-trihydroxystilbene,
2,4,4'-trihydroxystilbene,
3,4,4'-trihydroxystilbene,
3,4',5-trihydroxystilbene,
2',3,4-trihydroxystilbene,
2,3',4-trihydroxystilbene,
2',2,4'-trihydroxystilbene,
2,4,4',5-tetrahydroxystilbene,
2',3,4',5-tetrahydroxystilbene,
2,2',4,4'-tetrahydroxystilbene,
3,3',4',5-tetrahydroxystilbene,
2,3',4,4'-tetrahydroxystilbene,
3,3',4,4'-tetrahydroxystilbene,
3,3',4',5,5'-pentahydroxystilbene,
2,2',4,4',6-pentahydroxystilbene,
2,3',4,4',6-pentahydroxystilbene,
2,2',4,4',6,6'-hexahydroxystilbene.

3,4',5-trihydroxystilbene (or resveratrol) is the preferred compound according to the invention.

The amount of hydroxystilbene which can be used according to the invention obviously depends on the desired effect and should be an amount which is effective for promoting desquamation of the skin and/or stimulating epidermal renewal and/or combating intrinsic and/or extrinsic skin aging.

For example, the amount of hydroxystilbene according to the invention advantageously ranges from 0.001% to 10% and preferably from 0.005% to 5% of the total weight of the composition.

The invention also features compositions for promoting desquamation of the skin and/or stimulating epidermal renewal and/or combating intrinsic and/or extrinsic skin aging, comprising an effective amount of at least one hydroxystilbene as described above formulated into appropriate cosmetically/dermatologically acceptable medium therefor (diluent, vehicle or carrier).

The hydroxystilbenes according to the invention are thus used as active agents to promote desquamation of the skin and/or stimulate epidermal renewal and/or combat intrinsic and/or extrinsic skin aging, in particular when formulated for hair use or in a composition for the skin of the body and/or of the face.

The subject compounds/compositions are advantageously formulated as an emulsion, especially an oil-in-water or water-in-oil emulsion, or even in the form of a multiple emulsion. They may also be provided in the form of an aqueous or aqueous/alcoholic or oily solution, optionally gelled, or in the form of a lotion, for example a two-phase lotion, an ointment, a cream, a milk or even a foam.

The compositions according to this invention may comprise an oily phase based on animal, vegetable, mineral, silicone, fluorinated and/or synthetic oil.

The oily phase may also comprise fatty alcohols or fatty acids, as well as surfactants.

Exemplary are the hydrocarbon oils such as paraffin oil or liquid petroleum jelly; perhydrosqualene, arara oil, sweet almond, calophyllum, palm, castor, avocado, jojoba, olive or cereal germ oil; alcohols such as oleyl alcohol, linoleyl or linolenyl alcohol, isostearyl alcohol or octyl dodecanol. Also exemplary are the silicone oils such as the PDMSs, optionally phenylated, such as phenyltrimethicones.

The oily phase may also comprise a makeup removing oil such as a fatty acid ester, in particular the esters prepared from a straight or branched chain alcohol having from 1 to 17 carbon atoms and from a straight or branched chain fatty acid having from 3 to 18 carbon atoms.

Representative such esters include dioctyl adipate, 2-ethylhexyl palmitate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate and isopropyl isostearate.

The oily phase advantageously constitutes an amount of 5% to 95% by weight in the case of an emulsion.

The compositions according to the invention may comprise, in addition:

(i) an agent effecting the suspension of the fatty phase, for example a copolymer of $C_{10}$–$C_{30}$ alkyl acrylates and acrylic or methacrylic acid or ester thereof (Pemulen TR1, Pemulen TR2, Carbopol 1342 marketed by GOODRICH); or an acrylamide/methylpropanesulfonic acid copolymer (Sepigel marketed by SEPPIC), and/or (ii) an agent for dispersing the fatty phase, such as an emulsifying or vesicular system based on vesicles, optionally of nanometric size, comprising ionic lipids (liposomes) or nonionic lipids, and in particular the emulsifying systems well known to the art and comprising of glyceryl stearate/PEG 100 stearate (CTFA), cetyl alcohol and stearyl alcohol.

The compositions of the invention too may comprise, in addition, an agent for modifying its viscosity, and to provide textures which are gelled to a greater or lesser degree, such as:

(iii) cellulose derivatives (carboxymethylcellulose, hydroxyethylcellulose, hydroxypropylmethylcellulose), (iv) natural gums such as xanthan, guar and carob gums, scleroglucans, chitin or chitosan derivatives, carrageenans, (v) polycarboxyvinyl derivatives of the Carbomer type (marketed by GOODRICH under the trademarks Carbopol, 940, 951, 980, or by 3V-SIGMA marketed under the trademarks Synthalen K or Synthalen L).

The compositions according to the invention may also comprise conventional additives and adjuvants for cosmetic/dermatological applications, such as preservatives, antioxidants, perfumes, fillers such as kaolin or starch, or even hollow microspheres, pigments, UV-screening agents, sequestrants, essential oils, odor absorber, colorants, hydrophilic or lipophilic active agents such as moisturizers, especially glycerin, butylene glycol, anti-inflammatory agents such as allantoin, bisabolol, anti-free radical agents such as vitamin E or derivatives thereof, soothing agents such as cornflower water, iris extract, depigmenting agents, biological active agents such as urea, amino acids, vitamins and derivatives thereof, proteins, salicylic acid and derivatives thereof, α-hydroxy acids, pyrrolidonecarboxylic acid and its salts, ceramides.

One skilled in this art will of course take care to select this or these optional additional additives and adjuvants, thereof, and/or quantity thereof, such that the advantageous properties of the compositions according to the invention are not, or not substantially, altered by the addition envisaged.

The subject compositions preferably have a pH which does not damage the skin, generally ranging from 5 to 8, preferably a pH ranging from 5.5 to 7.5.

In order to further illustrate the present invention and the advantages thereof, the following specific examples are given, it being understood that same are intended only as illustrative and in nowise limitative.

EXAMPLE 1

The capacity of resveratrol to promote desquamation of the skin was examined

This test of the in vitro effect of an active agent on desquamation was carried out on differentiated human keratinocytes. The principle of the test was based on the fact that desquamation induces the release of corneocytes. The higher the number of corneocytes released, the greater the desquamation power of the product tested.

The protocol for the test was the following: starting with human skin biopsies, the keratinocytes obtained by separating the epidermis were dissociated by enzymatic action with trypsin and placed in culture at the concentration of $2 \times 10^5$ cells/ml. The growth and differentiation of the keratinocytes was obtained by culturing for 10 to 20 days in a specific medium. The activity of the test product was then evaluated after removing the culture medium. To do this, two samples were collected at T0 and T60, namely, before the addition of the product and 60 minutes after this addition. The samples thus collected were analyzed by flow cytometry in order to count the corneocyte population. The flow cytometry made it possible to distinguish the corneocyte and keratinocyte populations by treating with acridine orange specific for the DNA in the cells. This staining was specific for the keratinocytes since normal corneocytes possess no nuclei and therefore no DNA.

The cellular detachment index was determined by the difference between T60 and T0. The same measurement was carried out for a control containing no test product because the experiment inevitably produced the release of corneocytes, even in the absence of active agents.

The results of these studies are reported in the following Table:

TABLE

|  | Control | Reference* $5 \times 10^{-5}$ M | Resveratrol $5 \times 10^{-5}$ M |
| --- | --- | --- | --- |
| Activity in % | 100 | 196.6 p < 0.05 | 188 p < 0.05 |

*Reference: 2-hydroxy-5-octanoylbenzoic acid known to promote desquamation (FR-85/06953 assigned to the assignee hereof)
Buffer: PBS buffer alone.
p: variance analysis - Dunnett's multiple comparison test.

The results are given as % activity relative to the control consisting of an identical culture in the absence of a compound.

The activity of resveratrol on cellular detachment was therefore substantial. This dose-dependent activity was close (in % equivalent) to that of the reference.

EXAMPLE 2

Examples of specific formulations according to the invention; these compositions were formulated simply by intimately admixing the various components

| Composition 1: Face milk | |
| --- | --- |
| Liquid petroleum jelly | 7.0 g |
| Resveratrol | 0.1 g |
| Glyceryl monostearate, polyethylene glycol stearate (100 EO) | 3.0 g |
| Carboxyvinyl polymer | 0.4 g |
| Stearyl alcohol | 0.7 g |
| Soya bean proteins | 3.0 g |
| NaOH | 0.4 g |
| Preservative | qs |
| Water | qs 100 g |

This composition was provided in the form of a face milk having good cosmetic properties and being soft and comfortable to use. The pH of the composition was about 5.5.

| Composition 2: Lotion | |
| --- | --- |
| Resveratrol | 0.5 g |
| 2-Ethylhexyl palmitate | 10.0 g |
| Cyclopentadimethylsiloxane | 20.0 g |
| Butylene glycol | 5.0 g |
| Preservative | qs |
| Water | qs 100 g |

This lotion, which contained no surfactant, promoted desquamation of the skin.

| Composition 3: Milk | |
| --- | --- |
| Octyl palmitate | 35.0 g |
| Glycerin | 2.0 g |
| Resveratrol | 0.8 g |
| $C_{10}$–$C_{30}$-acrylates/alkyl acrylates crosslinked polymer | 0.1 g |
| Triethanolamine | 0.1 g |
| Wheat amino acids | 1.0 g |
| Preservative | qs |
| Water | qs 100 g |

The milk obtained, which contained no surfactant, had good cosmetic properties.

| Composition 4: Face gel | |
| --- | --- |
| Glycerin | 10.0 g |
| Resveratrol | 1.0 g |
| Disodium cocoamphodiacetate | 1.0 g |
| Preservative | qs |
| Water | qs 100 g |

The gel obtained had good cosmetic properties.

| Composition 5: Water-based cleansing gel | |
| --- | --- |
| Butylene glycol | 7.0 g |
| Sodium lauroyl sarcosinate | 4.0 g |
| Resveratrol | 5.0 g |
| Triethanolamine | 0.8 g |
| Carbomer | 0.5 g |
| Preservative | qs |
| Water | qs 100 g |

The gel obtained had good cosmetic properties.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method of cosmetic or dermatological treatment for promoting at least one of desquamation or stimulating epidermal renewal of the skin of a human subject in need of said treatment, comprising topically applying thereto, for a period of time as required to elicit the desired response, a therapeutically effective amount of at least one hydroxystilbene.

2. A method of treatment as defined by claim 1 for promoting desquamation of the skin of a human subject in need of said treatment, comprising topically applying thereto, for a period of time as required to elicit the desired response, a desquamation-effective amount of at least one hydroxystilbene.

3. A method of treatments defined by claim 1 for stimulating renewal of the epidermal skin of a human subject in need of said treatment, comprising topically applying thereto, for a period of time as required to elicit the desired response, an epidermal renewal-effective amount of at least one hydroxystilbene.

4. The method of treatment as defined by claim 1, which does not result in sensations pricking, twitching, overheating, or redness sensations of the skin.

5. A method of treatment as defined by claim 1, said at least one hydroxystilbene having the structural formula (I), or a hydroxyalkylated derivative thereof:

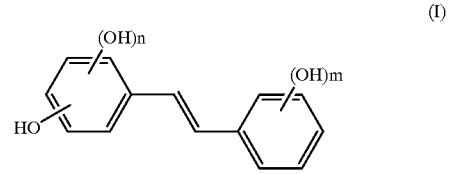

wherein n is integer ranging from 0 to 4 and m is an integer ranging from 0 to 5.

6. The method of treatment as defined by claim 5, said at least one hydroxystilbene being selected from the group consisting of 4'-hydroxystilbene, 2',4'-dihydroxystilbene, 3',4'-dihydroxystilbene, 4,4'-dihydroxystilbene, 2',4',4-trihydroxystilbene, 3',4',4-trihydroxystilbene, 2,4,4'-trihydroxystilbene, 3,4,4'-trihydroxystilbene, 3,4',5-trihydroxystilbene, 2',3,4-trihydroxystilbene, 2,3',4-trihydroxystilbene, 2',2,4'-trihydroxystilbene, 2,4,4',5-tetrahydroxystilbene, 2',3,4',5-tetrahydroxystilbene, 2,2',4,4'-tetrahydroxystilbene, 3,3',4',5-tetrahydroxystilbene, 2,3',4,4'-tetrahydroxystilbene, 3,3',4,4'-tetrahydroxystilbene, 3,3',4',5,5'-pentahydroxystilbene, 2,2',4,4',6-pentahydroxystilbene, 2,3',4,4',6-pentahydroxystilbene, and 2,2',4,4',6,6'-hexahydroxystilbene.

7. The method of treatment as defined by claim 6, wherein said at least one hydroxystilbene is 3,4',5-trihydroxystilbene.

8. The method of treatment of claim 1, wherein said hydroxystilbene is contained in a cosmetic/dermatological composition containing from 0.001% to 10% by weight thereof.

9. The method of treatment of claim 8, wherein said hydroxystilbene amount ranges from 0.05% to 5% by weight.

10. The method of treatment of claim 1, wherein the topically administered hydroxystilbene is contained in a composition selected from the group consisting of an aqueous composition, aqueous/alcoholic or oily solution, emulsion, aqueous or oily gel, dispersion, and lipid vesicles.

11. The method of treatment of claim 1, wherein said topically administered hydroxystilbene is in a composition selected from the group consisting of a cream, ointment, milk lotion and a foam.

12. The method of treatment of claim 1, wherein said topically administered hydroxystilbene is further administered in combination with another compound selected from the group consisting of at least one hydrophilic or lipophilic active agent, preservative, antioxidant, perfume, filler, UV-screening agent, essential oil, anti-inflammatory agent, colorant, chelating agent, odor absorber, anti-free radical agent, depigmenting agent, urea, amino acid, soothing agent, vitamin, protein, salicylic acid or derivative thereof, α-hydroxy acid, ceramide, pyrrolidonecarboxylic acid, and combinations thereof.

* * * * *